United States Patent [19]

Massie et al.

[11] Patent Number: 5,055,492
[45] Date of Patent: Oct. 8, 1991

[54] METHOD FOR AFFECTING REPRODUCTIVE CYCLE OF INSECTS

[75] Inventors: Harold R. Massie, New Hartford; Trevor R. Williams, Petersboro, both of N.Y.

[73] Assignee: Masonic Medical Research Laboratory, Utica, N.Y.

[21] Appl. No.: 921,390

[22] Filed: Oct. 22, 1986

Related U.S. Application Data

[63] Continuation-in-part of Ser. No. 744,683, Jun. 14, 1985, abandoned.

[51] Int. Cl.$^5$ .............................................. A01N 37/00
[52] U.S. Cl. ...................................... 514/553; 424/78; 424/81; 514/578
[58] Field of Search .................. 514/553, 578; 424/78, 424/81

[56] References Cited

U.S. PATENT DOCUMENTS

| | | | |
|---|---|---|---|
| 3,725,553 | 4/1973 | Giotti et al. | 514/578 |
| 3,906,107 | 9/1975 | Somani et al. | 514/578 |
| 3,920,833 | 11/1975 | Cook et al. | 514/578 |
| 4,298,613 | 11/1981 | Lepone | 514/417 |

FOREIGN PATENT DOCUMENTS

| | | | |
|---|---|---|---|
| 3189M | 3/1965 | France | 514/578 |
| 0102822 | 9/1974 | Japan | 514/578 |
| 0140017 | 8/1983 | Japan | 514/578 |
| 1430157 | 3/1976 | United Kingdom | 514/578 |

OTHER PUBLICATIONS

Chemical Abstracts 89:71465d (1978).
King; Chemicals Evaluated as Insecticides and Repellents at Orlando, Fla., May 1954, pp. 1-7, 320+321.

*Primary Examiner*—Allen J. Robinson
*Attorney, Agent, or Firm*—Darby & Darby

[57] ABSTRACT

The reproductive cycle of insects is affected by applying a solution or suspension of a material having the formula:

$$NX_2(CX_2)_mSO_3Z,$$

where each X is selected from the group consisting of H, OH, $C_nH_{2n+1}$, $C_nH_{2n}$, Cl, Br, and I; Z is selected from the group consisting of H, K, and Na; and n and m are integral numbers of from 2 to 10. Preferably, the compound applied for control of the insect reproductive cycle is taurine. The material may also be mixed with fruits. The concentration of the material should be at least 0.04M.

16 Claims, No Drawings

METHOD FOR AFFECTING REPRODUCTIVE CYCLE OF INSECTS

CROSS REFERENCE TO RELATED APPLICATION

This application is a continuation in part of prior application Ser. No. 744,683, filed June 14, 1985, now abandoned, by Harold R. Massie and Trevor R. Williams for "METHOD FOR AFFECTING REPRODUCTIVE CYCLE OF INSECTS," assigned to the same Assignee as the present invention.

BACKGROUND OF THE INVENTION

One of the greatest problems of modern day agriculture is the prevention of damage caused to growing crops by insects. This insect damage can interfere with the growth of crops, or may involve the destruction of the crops so as to prevent salability.

For example, and a frequent subject of recent publicity, is the destruction of crops by fruit flies. While various products are sold to deal with this insect infestation in the form of insecticides and pesticides, the treatments are frequently effective only cosmetically. While insects are destroyed at a particular phase of the life cycle, the reproductive cycle of the insect is not affected, and subsequent generations of the same insect appear to repeat the crop damage experienced.

Thus, repeated applications of the insecticides of the present state of the art are required on an annual, or even more frequent basis. Frequently, after a number of years, the insect damage is not even reduced, as the insects build up a tolerance and resistance to the particular insecticide and, while in some cases stronger doses are an aid, in other cases an entirely new product must be employed.

The industry has long sought a product which, after one, or only a few applications, would rid an entire area of the particular insect plague, so that repeated applications would not be required. Obviously, an insecticide which would interfere with the reproductive cycle of the insect, preventing the appearance of future generations of that insect would be most useful. To some extent, such a system has been tried and found successful when sterile insects of the particular specie to be eliminated are freed into an area to mate with the destructive insects and thus prevent reproduction. Such systems have met with limited success.

Obviously, a far more useful system would involve a chemical treatment which would interfere with the reproductive cycle of the insect and, thus, prevent the appearance of future generations of the insect. More particularly, such a treatment which would involve the use of natural materials would be most beneficial. To date, such treatments have not been available.

Similarly, animals are severely affected by insects, in many cases disease bearing insects, such as flies and mosquitos. Most often, with animals, such as cattle, the insects are attracted to the feed. Treatment of the animal feed with a material which would interfere with the reproductive cycle of the insect, while having no adverse effect on the animal or, in the case of food animals, upon humans, would be extremely desirable.

An article by B. Hue, M. Pelhate and J. Chanelet in *Taurine and Neurological Disorders*, edited by A. Barbeau and R. J. Huxtable, Raven Press, New York 1978, entitled "Sensitivity of Postsynaptic Neurons of the Insect Central Nervous System to Externally Applied Taurinez" refers to the use of taurine on isolated cockroach neurons. However, the amount of taurine employed is only 0.02M, while, as will be shown in this application, such an amount is insufficient to accomplish the desired results. Further, the insects treated in accordance with the referenced article were adult insects, while the present application is meant for treatment of insects in the egg stage.

SUMMARY OF THE INVENTION

In accordance with the present invention, it has unexpectedly been discovered that application of a solution or suspension of a material having the formula:

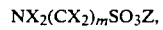
$NX_2(CX_2)_mSO_3Z$, where each X is independently selected from the group consisting of H, OH, $C_nH_{2n+1}$, $C_nH_{2n}$, Cl, Br, and I; Z is selected from the group consisting of H, K, and Na; m is an integral number of from 2 to 10; and n is from 2 to 10; when applied to or mixed with plants and fruits, sufficiently interrupts the reproductive cycle of the insect that the insect is removed as a source of harm to plant or to animals eating the fruits. "Fruits" is used in the dictionary sense as "any plant product, as grain, flax, vegetables, etc." Preferably, because it is a natural product, found in many places in nature, and is non-mutatable, taurine, where each X is H, Z is H, and m is 2, is the preferred material.

The material of the generic formula can be applied to the plant or fruit as by spraying from aqueous or alcoholic solutions, where the solutions may also contain natural or artificial sugars, or may be mixed with the fruits. The method of spraying and the particular constituency of the carrier form no part of the present invention but are determined by the one applying the treatment based upon the area to be covered, the equipment available, and other extrinsic factors.

Not only is the material of the present invention useful in the control of fruit flies and mosquitos, but, generally, for control of all flies within the order Diptera. The materials of the present invention are also useful for control of insects of the order Siphonaptera, which have a developmental stage similar to members of the order Diptera. It is believed that the material of the present invention would generally be employable for treatment of all insects.

DESCRIPTION OF THE PREFERRED EMBODIMENTS

Plants and fruits are protected from insect destruction by applying to the plant, or mixing with the fruits, a solution of a material having the formula:

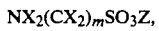
$NX_2(CX_2)_mSO_3Z$, where each X is selected from the group consisting of H, OH, $C_nH_{2n+1}$, $C_nH_{2n}$, Cl, Br, and I; Z is selected from the class consisting of H, K, and Na; and n and m are integral numbers of from 2 to 10. A preferable way to form the treatment solution is to form a one molar concentration of the product and then dissolve it in a mixture of water and a medium for binding the aminosulfonic acid or salt to the product being protected. For example, glycerine, which forms a sticky surface for the adherence of the aminosulfonic acid to the plant tissue would be a preferred material. When employed as a solution, the minimum concentration of the material of the generic formula, particularly taurine, to be employed, is 0.04M. Preferably, the concentration is at least 1M. When harvested fruits are to be treated with a solution of the material in accordance with the present invention, again, a minimum solution concentration of 0.04M should be employed, preferably at least 1M. When the materials employed in accordance with the present invention are mixed with fruits and grains, such as in animal feed and grain storage, the equivalent of a 0.04M concentration would be the minimum employed; for example, approximately 5 grams of solid taurine powder would be employed for each kilogram of grain or feed.

When employing the material in accordance with the present invention as a solution, in addition to glycerine, other materials could be employed, including such inert polymers as pectin, hydroxyethyl-cellulose, hydroxyethyl starch, dextran, polyhydroxyethyl-methacrylate, copolymers of lactic or glycolic acid, etc. The amount of water to be included in the overall composition could vary from 0 to 100%, depending upon the equipment employed for application and the area to which the application is to be made. The inert polymer is generally employed to improve the clinging properties of the solution onto the plant, and is not believed to take an active part in the curbing of insecticidal activity. Consequently, the molecular weight or viscosity of the inert polymer is not deemed critical, but is determined based upon the use and method of application.

Within the generic formula set forth above, the possible substituents in the composition are preferably shorter chain materials, such as hydroxyl, methyl, ethyl, and hydrogen; hydrogen is most preferred. The most preferred product of the generic formula is taurine, where each X is hydrogen, Z is hydrogen, and m is 2. As previously indicated, taurine is a natural product and is found in various situations. As a consequence, it is believed that the ability of an insect specie to mutate against it is severely reduced, thus improving its efficacy Further, since taurine is generally non-toxic and water soluble, its use in connection with foods for human consumption is indicated.

Though, in the example below, the use of the aminosulfonic acids of the present invention are employed for interrupting the reproductive cycle of fruit flies, the use of the materials for interruption of reproductive cycles of all members of the class Insecta is indicated, particularly members of the orders Diptera and Siphonaptera, most particularly members of the order Diptera. The members of the order Diptera include tsetse flies, black flies, mosquitos, fruit flies, blowflies, and house flies.

The following examples illustrate the utilization of the method of the present invention:

EXAMPLE 1

A one molar aqueous solution of taurine was prepared in 20% glycerine. Bananas were dipped into the solution such that the skin of the fruit was completely covered. Five hundred fruit flies, half male and half female, were introduced into a container with the whole fruit and allowed to lay eggs for 24 hours. The fruit was then removed from the containers and transferred to clean containers having no fruit flies and monitored for development of larva and flies. Bananas which were not treated with the taurine solution were similarly placed in containers into which five hundred fruit flies, half male and half female were placed, and were removed after 24 hours and placed into clean containers.

Visual observation indicated an absence of eggs laid on the bananas which had been treated with the taurine solution, while clumps of eggs were observed on the untreated bananas.

After six days, no larval development was noted on the treated bananas, while some activity was seen on the untreated bananas. After an additional week, the experimental bananas showed neither flies nor larva, while larval development on the control bananas was evident.

EXAMPLE 2

The procedure of Example 1 was followed employing grapes, rather than bananas. Upon removal of the grapes from the containers, the treated grapes showed no visible eggs, while the control grapes, which had not been treated with taurine solution, showed large clumps of eggs.

After one week, no larval development was seen on the grapes which had been treated with the taurine solution, while larva were abundant on the grapes which had not been so treated. Further, the grapes which had been treated with the taurine solution show a heavy growth of what appeared to be yeast, a further indication of either a lack of egg deposit or immediate death of the larvae upon hatching.

After an additional week, the untreated grape container showed hundreds of flies, with more larva developing. The grapes which had been treated with taurine solution showed less than half a dozen flies present in the container, and no larva visible. It is probable that, after treatment, one of the grapes split slightly, allowing the development of the half dozen flies seen in the treated grapes.

EXAMPLE 3

Taurine was mixed with a fruit fly medium known as corn meal medium to obtain a final taurine concentration of 0.04M. Corn meal medium is formed from 7.6 gm. granulated agar (Teklad Test Diets), 173.2 ml. Grandma's molasses, 144.7 gm. yellow corn meal (Quaker Oats), 29.6 gm. non-fat dry milk (Carnation), 70 gm. sucrose (Red and White), 7.6 gm. dry powdered yeast (Natural Brands) in one liter of water. Five hundred fruit fly eggs were placed into a container with the treated corn meal medium. There was no development of fruit flies.

EXAMPLE 4

A corn meal medium containing 0.06M taurine was formed in the same manner and tested in the same manner as in Example 3. Again, there was no development of fruit flies.

EXAMPLE 5

Tests were run in the same manner as Examples 3 and 4 employing 0.02M taurine and no taurine. Within a week adult fruit flies had completed emerged.

It will thus be apparent that at least a concentration of 0.04M of the material of the present invention is required in order to prevent the development of adult insects. When the concentration is below 0.04M, as in Example 5, adult insects develop. Use of the material of the present invention in a solution are shown, as in Examples 1 and 2, and in a feed type medium, as in Examples 3 and 4, with equally effective results.

Similar results to those specifically shown and described are obtained when the treatment is employed for other fruits and for growing plants, as well as when the treatment is applied to other insects, particularly insects of the orders Diptera and Siphonaptera, most particularly insects of the order Diptera.

While the method of the present invention is applicable to fruits, generally, it is believed particularly applicable to protect or disinfect from insect contamination apples, oranges, pears, figs, apricots, grapes, bananas, papayas, grains, and meal. Among the materials which would fall into the definition of meal are stored wheat, corn, rice, and animal feeds.

Based upon the above, it is apparent that use of aminosulfonic acids of the formula:

$$(NX_2(CX_2)_m SO_3Z,$$

where each X is selected from the group consisting of H, OH, $C_nH_{2n+1}$, $C_nH_{2n}$, Cl, Br, and I; Z is selected from the group consisting of H, K, and Na, and n and m are integral numbers of from 2 to 10, particularly taurine, is effective in interrupting the reproductive cycle of insects. The material can be employed in treatment of animal feeds, as well as for plant treatment, and in other areas where insect control is indicated.

The invention should not be considered as limited to the examples shown and described, but only as set forth in the appended claims.

We claim:

1. A method for interrupting the reproductive cycle of insects comprising:
   a. forming an aqueous solution of an aminosulfonic acid having the formula:

$$NX_2(CX_2)_m SO_3Z,$$

where each X is selected from the group consisting of H, OH, $C_nH_{2n+1}$, $C_nH_{2n}$, Cl, Br, and I; Z is selected from the group consisting of H, K, and Na, and n and m are integral numbers of from 2 to 10; the concentration of said aminosulfonic acid in said aqueous solution being at least 0.04M; and
   b. applying said solution to a plant subject to insect attack.

2. The method of claim 1 wherein X is selected from the group consisting of hydrogen, hydroxyl, methyl, and ethyl.

3. The method of claim 1 wherein the aminosulfonic acid is taurine.

4. The method of claim 1 wherein said aqueous solution contains, in addition to said aminosulfonic acid, an inert polymer selected from the group consisting of glycerine, pectin, hydroxyethylcellulose, hydroxylethyl starch, dextran, and polyhydroxyethylethacrylate.

5. The method of claim 4 wherein the inert polymer is glycerine.

6. The method of claim 1 wherein the insects are selected from the orders Diptera and Siphonaptera.

7. The method of claim 6 wherein the insects are selected from the order Diptera.

8. The method of claim 7 wherein the insects are elected from the group consisting of fruit flies and mosquitos.

9. A method for interrupting the reproductive cycle of fruit flies comprising:
   a. forming an aqueous solution of an aminosulfonic acid having the formula:

$$NX_2(CX_2)_m SO_3Z,$$

where each X is selected from the group consisting of H, OH, $C_nH_{2n+1}$, $C_nH_{2n}$, Cl, Br, and I; Z is selected from the group consisting of H, K, and Na, and n and m are integral numbers of from 2 to 10; the concentration of said aminosulfonic acid in said aqueous solution being at least 0.04M; and
   b. applying said solution to a plant subject to insect attack.

10. The method of claim 9 wherein X is selected from the group consisting of hydrogen, hydroxyl, methyl, and ethyl.

11. The method of claim 9 wherein the amino acid is taurine.

12. The method of claim 9 wherein said aqueous solution contains, in addition to said aminosulfonic acid, an inert polymer selected from the group consisting of glycerine, pectin, hydroxyethylcellulose, hydroxyethyl starch, dextran, polyhydroxyethylmethacrylate, and copolymers of lactic or glycolic acid.

13. The method of claim 12 wherein the inert polymer is glycerine.

14. A method for interrupting the reproductive cycle of insects comprising mixing with an animal feed an aminosulfonic acid having the formula:

$$NX_2(CX_2)_m SO_3Z,$$

where each X is selected from the group consisting of H, OH, $C_nH_{2n+1}$, $C_nH_{2n}$, Cl, Br, and I; Z is selected from the group consisting of H, K, and Na, and n and m are integral numbers of from 2 to 10; the concentration of said aminosulfonic acid in said animal feed being at least 0.04M.

15. The method of claim 14 wherein X is selected from the group consisting of hydrogen, hydroxyl, methyl, and ethyl.

16. The method of claim 14 wherein the amino acid is taurine.

* * * * *